(12) United States Patent
Katsingris

(10) Patent No.: US 8,859,840 B2
(45) Date of Patent: Oct. 14, 2014

(54) MULTIPLE-USE BLOOD BLOTTING DEVICES FOR DIABETICS FOR USE WHEN MONITORING BLOOD GLUCOSE LEVELS

(76) Inventor: Cynthia Katsingris, Westfield, NJ (US)

( * ) Notice: Subject to any disclaimer, the term of this patent is extended or adjusted under 35 U.S.C. 154(b) by 534 days.

(21) Appl. No.: 13/227,683

(22) Filed: Sep. 8, 2011

(65) Prior Publication Data

US 2013/0066251 A1    Mar. 14, 2013

(51) Int. Cl.
  *A61F 13/00*    (2006.01)
  *B65G 59/00*    (2006.01)
  *A61F 13/20*    (2006.01)

(52) U.S. Cl.
  CPC .................................. *A61F 13/2002* (2013.01)
  USPC .................. 604/378; 435/2; 435/374; 221/5; 221/92

(58) Field of Classification Search
  CPC ............. A61B 17/00234; A61B 19/42; A61B 2017/320012; A45D 40/28; A61F 13/02; A61F 13/20; A61F 13/38; A61F 13/15203; A61F 13/2048; A61F 13/2051; A61F 13/206; A61F 13/2085; A61F 13/47209; A61F 13/49001; A61F 13/49003; A61F 13/495; A61F 13/511; A61F 13/53; A61F 13/534; A61F 13/535; A61F 13/539; A61F 13/551; A61F 13/5514; A61F 13/55175; A61F 13/58; A61F 13/84; A61K 8/0208; A61L 15/18; A61L 15/28; A61M 31/00; A61M 35/00; A61M 35/003; A61M 35/006; A61M 37/00

USPC ............. 604/1, 289, 290, 358, 367–370, 374, 604/377, 384, 385.01, 385.02; 221/2, 4, 5, 221/8, 92, 98, 99, 103, 105, 112, 114, 156, 221/161, 171, 186, 191, 197, 206, 207, 209, 221/236, 237
  See application file for complete search history.

(56) References Cited

U.S. PATENT DOCUMENTS

| | | | |
|---|---|---|---|
| 4,572,376 A * | 2/1986 | Wrennall | ....................... 206/538 |
| 4,799,488 A | 1/1989 | Mintz | |
| 5,830,170 A | 11/1998 | Whiteman et al. | |
| 6,835,864 B2 | 12/2004 | Luck | |
| 7,780,615 B1 | 8/2010 | Shesol | |
| 2007/0265511 A1 | 11/2007 | Renouf | |
| 2009/0246750 A1 * | 10/2009 | Lloyd et al. | ....................... 435/2 |
| 2012/0093759 A1 * | 4/2012 | Vachon | ....................... 424/78.1 |

* cited by examiner

*Primary Examiner* — Melanie Hand
(74) *Attorney, Agent, or Firm* — Doherty IP Law Group LLC

(57) ABSTRACT

A multiple-use blotting device for blotting blood from a fingertip includes a substrate, and a blood absorbing pad secured to the substrate. The blood absorbing pad has a plurality of blood absorbing sections that are evenly spaced from one another. The blotting device includes a protective cover overlying the blood absorbing pad, the protective cover having a window formed therein for exposing the blood absorbing pad. The cover is coupled with the substrate and is adapted to rotate relative to the substrate and the blood absorbing pad for sequentially aligning the window of the cover with each of the blood absorbing sections for exposing, one at a time, each of the blood absorbing sections. After one section of the pad has been used to blot blood, the cover is rotated for exposing a clean, unused section of the pad, while covering the used, blood-soaked section of the pad.

18 Claims, 10 Drawing Sheets

MULTIPLE-USE BLOOD BLOTTING DEVICES FOR DIABETICS FOR USE WHEN MONITORING BLOOD GLUCOSE LEVELS

BACKGROUND OF THE INVENTION

1. Field of the Invention

The present invention generally relates to medical devices for blotting blood, and more particularly relates to blood blotting devices for blotting blood on fingertips.

2. Description of the Related Art

Diabetes afflicts millions of people throughout the United States. This number is projected to grow as the population lives longer and grows older.

There are several types of diabetes. The two main types of diabetes are Type 1 and Type 2. Type 1, formerly called juvenile on-set diabetes, typically occurs before 20 years of age. Individuals with Type 1 diabetes have a pancreas, the organ that secretes insulin, which is destroyed by auto-antibodies. That is why individuals with Type 1 diabetes always need insulin, either through an injection or through an insulin pump. The role of insulin is to move glucose from the bloodstream into muscle, fat and liver cells where it can be used as fuel. Sugar levels reach dangerous levels when insulin is not present.

Type 1 diabetics must continuously monitor glucose levels in order to ensure health. Blood glucose or finger stick testing is required on a daily basis, usually before and after all meals, upon waking if breakfast is not immediately available, and when going to bed. Without constant glucose monitoring, the diabetic has no idea how much insulin is needed to maintain a safe range of glucose in the blood. Failure to monitor blood glucose levels can result in diabetic comas and even death. Long term failure to maintain tight control of blood glucose levels leads to blindness, kidney failure and nerve disease or neuropathy which commonly leads to amputations.

Type 2 diabetes, often referred to as adult on-set diabetes, is usually diagnosed after the age of 35. However, each year nearly 4,000 children are diagnosed with Type 2 diabetes, and children who develop Type 2 diabetes by age 9 typically require insulin by the time they reach age 18. The primary cause of Type 2 diabetes is a complex medical condition called "insulin resistance." In the early stages of Type 2 diabetes, the individual has sufficient insulin in the body; it just does not work efficiently. Type 2 diabetes is often treated through diet, exercise, and oral medications, however, it is not uncommon for an individual with Type 2 diabetes to eventually need insulin, either with or without oral medications. Blood glucose or finger stick testing is also required on a daily basis when treating Type 2 diabetes.

Control and outcomes of both Type 1 and Type 2 diabetes is greatly improved in patients using home glucose meters to regularly measure their glucose levels. According to some medical protocols, Type I diabetics must test their blood glucose levels at least five times per day, and Type II diabetics must test their blood glucose levels at least twice a day. In some cases, blood glucose levels in diabetics fluctuate wildly, so that the blood must be tested every half hour. Typically, a blood glucose level test requires a patient to prick a fingertip for drawing blood. Unfortunately, the testing procedure is invasive and results in bleeding. This requires diabetic patients to frequently swab or blot the test site with a swab, tissue or other absorbent material to remove the blood present on the fingertip.

Diabetic patients are required to carry kits that contain testing equipment for measuring blood glucose levels. Extreme care must be taken to avoid contaminating the testing equipment. As such, after pricking the end of a fingertip and applying the blood drops to the testing equipment, the patient must obtain a swab or tissue to blot the blood present on the fingertip. If the blood is not properly disposed of, the blood may contaminate the testing equipment, create an unsanitary condition, or cause an unsightly stain on clothing.

There have been a number of attempts directed to providing blood collecting devices for use with blood glucose level testing equipment. For example, U.S. Pat. No. 5,830,170 to Whiteman et al. discloses a blood-blotting device that includes a sheet of base stock having a plurality of fingertip-sized recesses formed therein with an absorbent swab disposed within each of the recesses. The swabs are relaseably attached to the recesses so that the soiled swabs may be removed after use. Lines of perforations may be formed in the sheets of base stock, allowing the sheet of base stock to be divided into sections, with each section including at least one recess and a swab. A protective sheet is attached to the sheet of base stock to cover and protect the swabs. The protective sheet has perforations that correspond to perforations in the sheet of base stock so that each of the swabs remains sterile and hygienic, even if the device is divided into small sections.

One drawback of the Whiteman device is that once a swab is used and removed from the base stock, the swab must be thrown away. In many instances, diabetic patients have no access to a refuse container for holding the contaminated swab. In these instances, the diabetic patient may place the contaminated swab back inside the diabetic testing kit, which may cause the unsanitary conditions described above, or which may contaminate the testing equipment.

In spite of the above advances, there remains a need for more efficient, multiple-use blood-blotting devices that facilitate the steps associated with testing blood glucose levels, which minimize contamination of the kit and the testing equipment, which improve sanitary conditions, which reduce the likelihood of blood stains on clothes, and which are easy to use. There also remains a need for blood-blotting devices that cover contaminated sections of a blood absorbing pad while exposing only unused sections of a blood absorbing pad.

SUMMARY OF THE INVENTION

In one embodiment, a multiple-use blotting device for blotting blood from a fingertip preferably includes a substrate, such as a substrate made of a polymer material, and a blood absorbing pad secured atop the substrate, the blood absorbing pad having a plurality of blood absorbing sections. In one embodiment, the blood absorbing pad may include cotton or fibrous material covered by a porous layer that enables blood to pass therethrough.

In one embodiment, the multi-use blotting device preferably includes a cover overlying the blood absorbing pad. The cover desirably has at least one window formed therein for exposing one of the blood absorbing sections at a time. The cover is preferably moveable (e.g. rotatable) relative to the blood absorbing pad for exposing only one of the blood absorbing sections at a time while covering the remaining blood absorbing sections.

In one embodiment, the blood absorbing sections provided on the pad are desirably spaced from one another on the blood absorbing pad. In one embodiment, the blood absorbing sections are preferably evenly spaced from one another around a perimeter of the blood absorbing pad. The cover may have various shapes. In one preferred embodiment, the cover has a circular shape. In one embodiment, the at least one window used for exposing the blood absorbing pad desirably extends between a center of the cover and an outer perimeter of the cover. In one embodiment, the cover may have two or more windows or openings, such as a first window for covering an inner region of the blood absorbing pad and a second window for exposing an outer region of the blood absorbing pad.

In one embodiment, the cover preferably includes a shell having at least one window formed therein. A knob is desirably provided on a top surface of the shell. The knob is preferably engageable by a user for selectively moving the shell for sequentially aligning the window with each of the blood absorbing sections. In one embodiment, the device also includes a shaft extending through the blood absorbing pad. The shaft preferably has an upper end coupled with the shell and a lower end coupled with the substrate. The cover, knob and shaft preferably rotate simultaneously with one another, and rotate relative to the blood absorbing pad and the substrate.

In one embodiment, the cover and the substrate are preferably made of polymer materials, such as plastic, and the blood absorbing pad is desirably made of absorbent materials such as cotton or fibrous materials. The blood absorbing pad preferably has an outer layer including a porous layer that enables blood to pass therethrough, which is preferably absorbed by the cotton or fibrous material core.

In one embodiment, the substrate desirably includes a top surface and the blood absorbing pad is secured to the top surface of the substrate. An adhesive or other form of securing element may be used for securing the blood absorbing pad of the substrate so that the blood absorbing pad does not move relative to the substrate.

In one embodiment, the blood absorbing pad may include an anti-bacterial agent, a germicidal agent, a disinfectant, and/or a moisturizer. In one embodiment, the blood absorbing pad may include all of the agents listed above, or a combination of two or more of the agents listed above.

In one embodiment, the substrate preferably has a side wall that extends around a perimeter of the substrate. A plurality of projections desirably extends outwardly from the side wall of the substrate. The cover preferably has an inner surface having at least one projection adapted to engage the side wall projections of the substrate when the cover is moveably mounted over the substrate. In one embodiment, when the cover is moved relative to the blood absorbing pad, the projections on the cover engage the projections on the substrate for generating an audible sound, such as a clicking sound, as the cover projection passes over the substrate projections. The cover and substrate may also have a tongue and groove interface for generating the audible indicator.

In one embodiment, the audible sound provides an audible indication of when the window of the cover has been rotated into alignment with the next blood absorbing section of the blood absorbing pad.

In one embodiment, a multi-use blotting device for blotting blood from a fingertip preferably includes a substrate having a top surface, and a blood absorbing pad secured over the top surface of the substrate, the blood absorbing pad having a plurality of blood absorbing sections that are evenly spaced from one another around the blood absorbing pad. The blotting device desirably includes a protective cover overlying the blood absorbing pad, the protective cover desirably including a window therein adapted to expose the blood absorbing pad. The cover is desirably coupled with the substrate and is adapted to rotate relative to the substrate and the blood absorbing pad for sequentially aligning the window with each of the blood absorbing sections.

In one embodiment, the blood absorbing pad and the protective cover preferably have circular shapes, respectively, and the window is located between a center of the protective cover and an outer perimeter of the protective cover. The protective cover is preferably moveable for exposing, one at a time, each of the blood absorbing sections through the window formed in the cover.

In one embodiment, the protective cover preferably includes a shell having a knob provided at a top surface of the shell. The device also preferably includes a shaft used for forming a rotatable connection between the shell and the substrate. The shaft desirably has an upper end coupled with the shell and a lower end coupled with the substrate. In one embodiment, the shaft preferably extends through the blood absorbing pad.

In one embodiment, the window on the cover is adapted for being rotated 360° around a center of the cover. In one embodiment, the window defines an arc of between about 15-40° of the 360° perimeter. In one embodiment, the blood absorbing pad has 10 blood absorbing sections and the window covers an arc of about 36°. In another embodiment, the blood absorbing pad has 20 blood absorbing sections and the window covers an arc of about 18°. In other embodiments, the blood absorbing pad may have fewer or more blood absorbing sections and the arc span of the window will be adjusted accordingly.

The multi-use blotting device disclosed herein is preferably adapted for being stored in a kit used for testing blood glucose levels. In one embodiment, the blotting device preferably has a diameter of about 3-5 inches and a thickness of about 0.10-1.00 inches.

In one embodiment, a multiple-use blotting device for blotting blood from a fingertip preferably includes a substrate having a top surface, and a blood absorbing pad secured over the top surface of the substrate, the blood absorbing pad having a plurality of blood absorbing sections that are spaced from one another on the blood absorbing pad. The device may include a protective cover overlying the blood absorbing pad, the protective cover having a plurality of windows formed therein that are associated with the plurality of blood absorbing sections of the blood absorbing pad. The device desirably has at least one sliding element disposed between the protective cover and the blood absorbing pad. The sliding element may be associated with a row of windows for selectively uncovering and covering sections of the blood absorbing pads associated with the respective windows. The sliding element is retractable from a first position to a second position for exposing at least one of the blood absorbing sections through at least one of the windows. After blood has been blotted, the sliding element is moveable from the second position back to the first position for re-covering the blood absorbing section exposed through the window.

The present invention provides an efficient and easy to use device for blotting blood from a fingertip. The device is preferably adapted for enhancing sanitation, eliminating unsightly blood soaked tissues, and eliminating the likelihood of blood contaminating testing equipment. The present invention also provides a portable device that may be readily stored within a testing kit for measuring blood glucose levels. The device preferably has minimal thickness so that it may be easily stored within a blood glucose level testing kit. In one embodiment, the device is preferably disposable so that it may be thrown away after all of the blood absorbing sections of the blood absorbing pad have been utilized. In one embodiment, the blood absorbing pad is preferably disposable for being replaced after being used and the cover and substrate are re-used with a replacement blood absorbing pad. In one embodiment, the cover or the sliding element preferably covers the sections of the blood absorbing pad that have been utilized, thereby blocking the unsightly, blood-stained sections from view.

These and other preferred embodiments of the present invention will be described in more detail herein.

DETAILED DESCRIPTION

Figure 1:
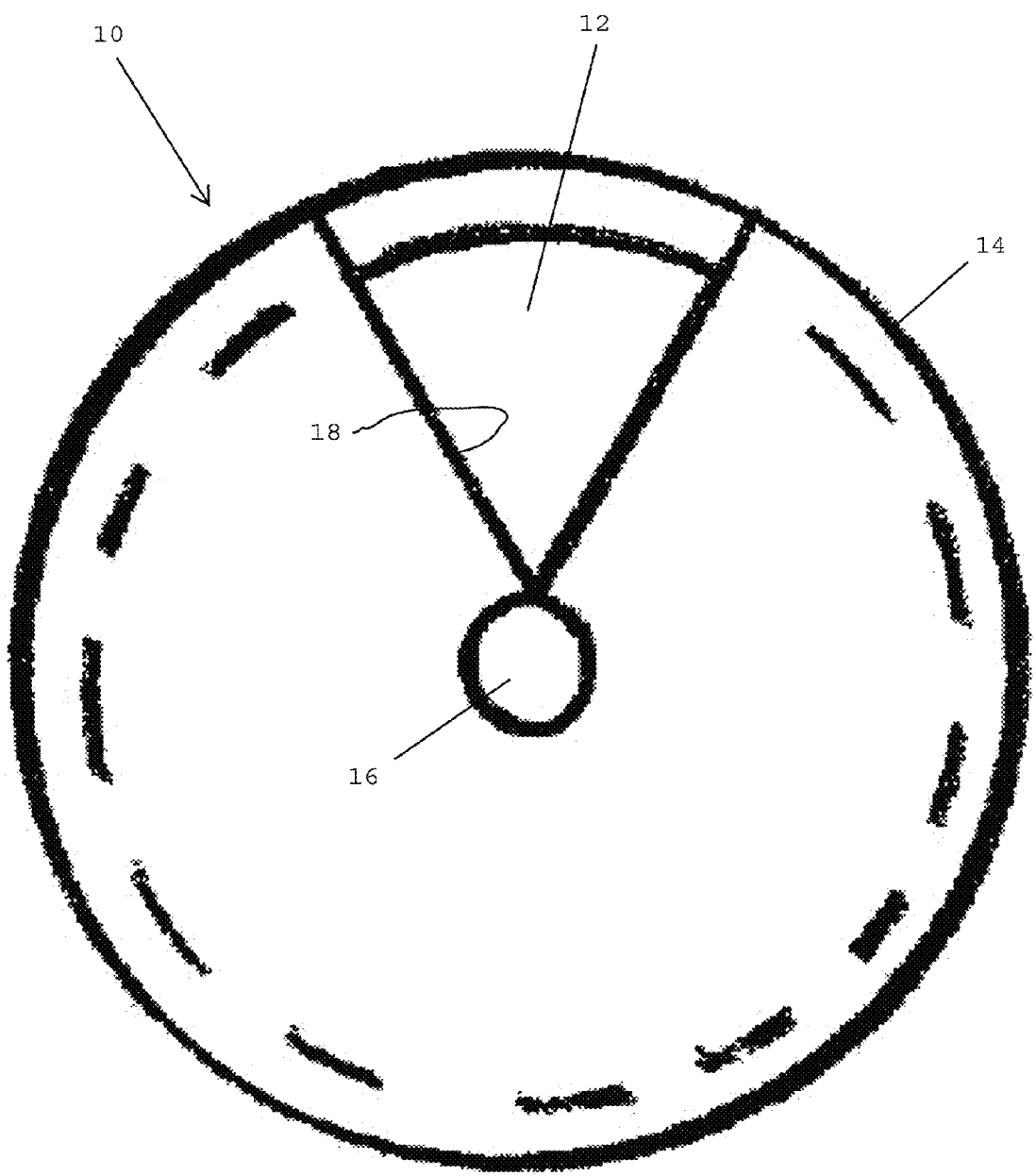
FIG. 1 shows a top plan view of a multiple-use blood-blotting device including a blood absorbing pad and a moveable cover overlying the blood absorbing pad, in accordance with one embodiment of the present invention.

FIG. 1 shows a multiple-use blood-blotting device used for blotting blood on fingertips. The blood-blotting device 10 preferably includes a blood absorbing pad 12 and a rotatable cover 14 that overlies the blood absorbing pad 12. The rotatable cover 14 preferably has a knob 16 that may be engaged for rotating the rotatable cover 14 relative to the blood absorbing pad 12. The rotatable cover desirably includes a window 18 formed therein that exposes a section of the blood absorbing pad. As will be described in more detail herein, the cover 14 may be rotated in clockwise or counter-clockwise directions relative to the blood absorbing pad 12 for exposing different sections of the blood absorbing pad through the window opening 18. After a section of the pad has been used for blotting blood, the cover may be rotated for covering the stained section of the pad, thereby eliminating an unsightly blood mark, and rotated to a fresh, unused section of the pad, which enhances the overall aesthetic appearance of the device. Covering the blood stained section of the pad also minimizes the likelihood that the blood will contaminate the testing equipment or the other items stored within the testing kit.

Figure 2A:
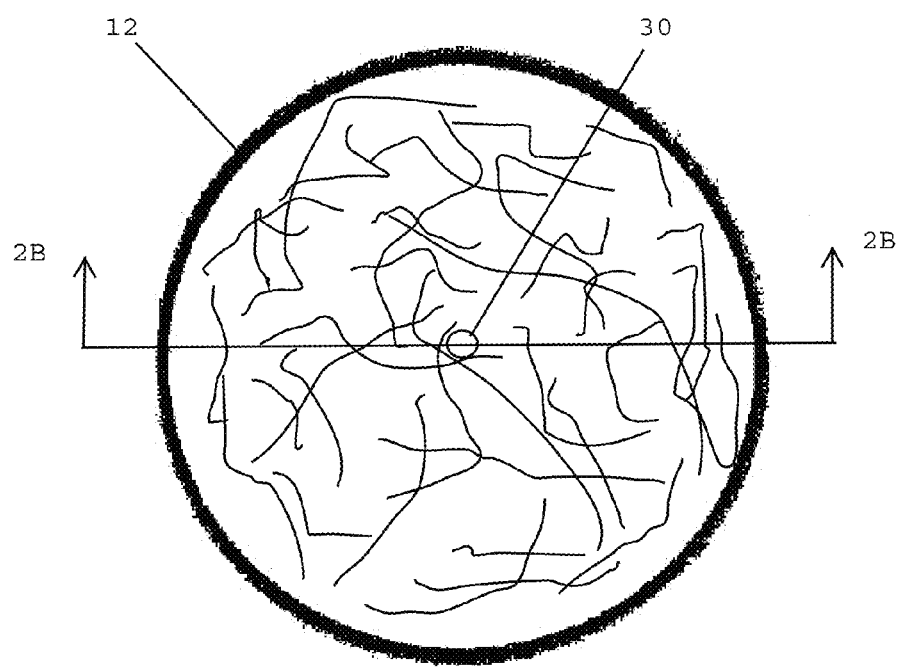
FIG. 2A shows a top plan view of the blood absorbing pad shown in FIG. 1.
Figure 2B:
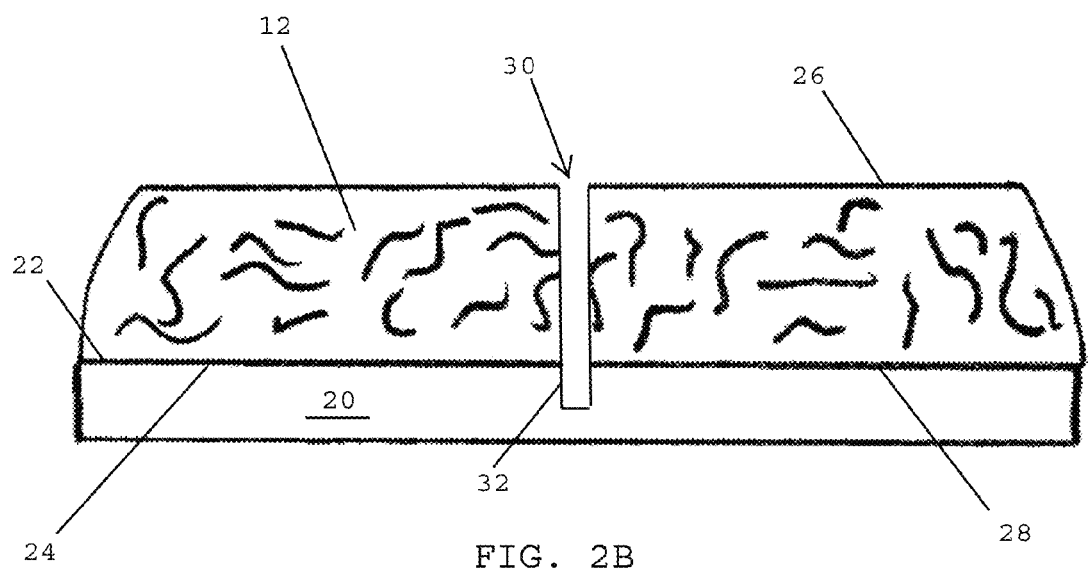
FIG. 2B shows a cross-sectional view of the blood absorbing pad of FIG. 2A taken along line 2B-2B thereof.

Referring to FIGS. 2A and 2B, in one embodiment, the blood-blotting device desirably includes the blood absorbing pad 12 mounted atop a substrate 20. The substrate preferably includes a top surface 22 and a bottom surface 24. In one embodiment, the top and bottom surfaces 22, 24 of the substrate 20 desirably extend within planes that are parallel to one another. The blood-blotting device 12 desirably has a top surface 26 and a bottom surface 28 that is secured to the top surface 22 of the substrate 20.

The blood absorbing pad desirably has a central opening 30 formed therein that extends from the top surface 26 to the bottom surface 28 thereof. A second central opening 32 is formed in the top surface 22 of the substrate 20. The first central opening 30 through the blood absorbing pad 12 and the second opening 32 formed in the substrate 20 are preferably aligned with one another.

The blood absorbing pad 12 is preferably made from an absorbent material that efficiently absorbs blood present on a fingertip. The pad 12 may be made of a material having anti-bacterial and/or germicidal properties. In one embodiment, the blood absorbing pad may be impregnated with a disinfectant, anti-bacterial agent, germicidal agent, or alcohol solution for providing a sanitary benefit. In one embodiment, the blood absorbing pads may contain a skin treatment solution such as a moisturizer. In one embodiment, the blood absorbing pad 12 may have a central region made of an absorbent material such as cotton and a cover made of a porous material such as mesh. The bottom surface 28 of the blood absorbing pad 12 may be adhered to the top surface 22 of the substrate 20 using an adhesive.

Figure 3A:
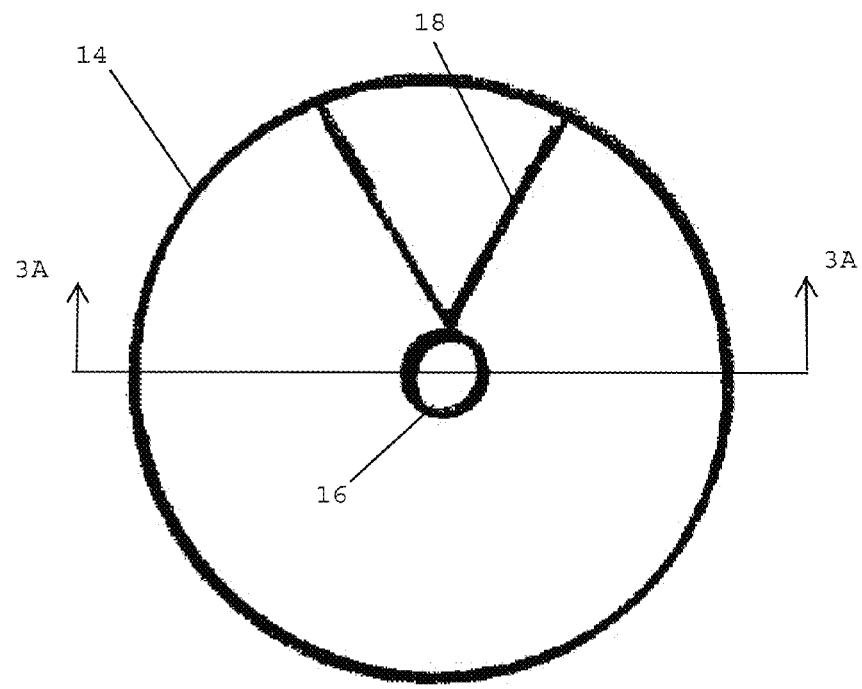
FIG. 3A shows a top plan view of the moveable cover shown in FIG. 1.
Figure 3B:
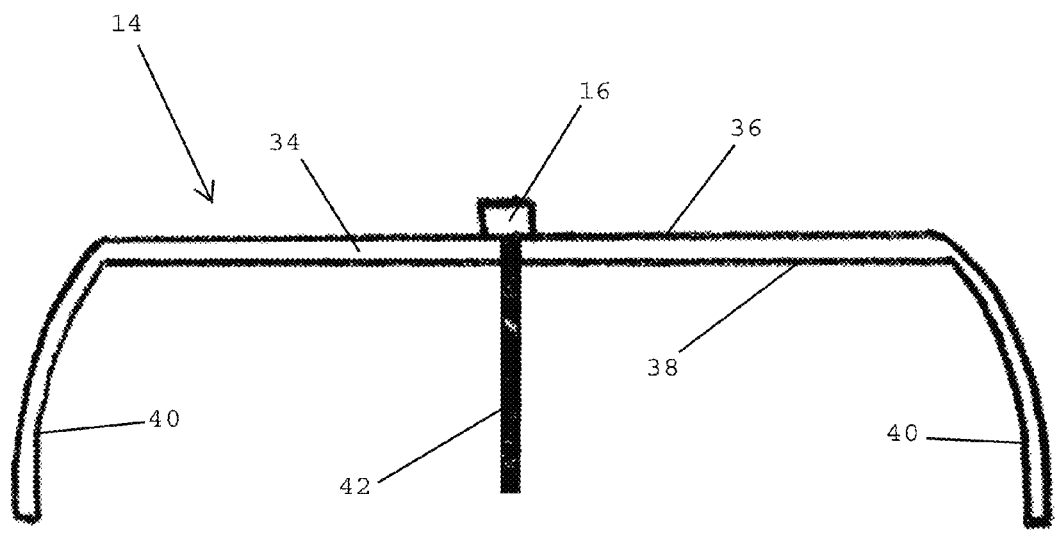
FIG. 3B shows a cross-sectional view of the rotatable cover of FIG. 3A taken along line 3B-3B thereof.

Referring to FIGS. 3A and 3B, in one embodiment, the rotatable cover 14 is adapted to overlie the blood absorbing pad and to be rotatable for exposing different sections of the blood absorbing pad. The rotatable cover 14 desirably includes a shell 34 having an exterior surface 36 and an interior surface 38. The shell 34 preferably includes a lateral region 40 that is adapted to cover the outer perimeter of the blood absorbing pad and the substrate.

The rotatable cover 14 preferably includes the knob 16 secured to the shell 34 and a shaft 42 having an upper end secured to the shell for rotating simultaneously with the shell. The rotatable cover 14 also desirably includes the window 18 that is adapted to provide access to a blood absorbing pad underlying the cover. In operation, an individual may engage the knob 16 for rotating the position of the window 18 relative to the underlying blood absorbing pad. The knob 16 and the shaft 42 rotate simultaneously with the cover 14.

Figure 4A:
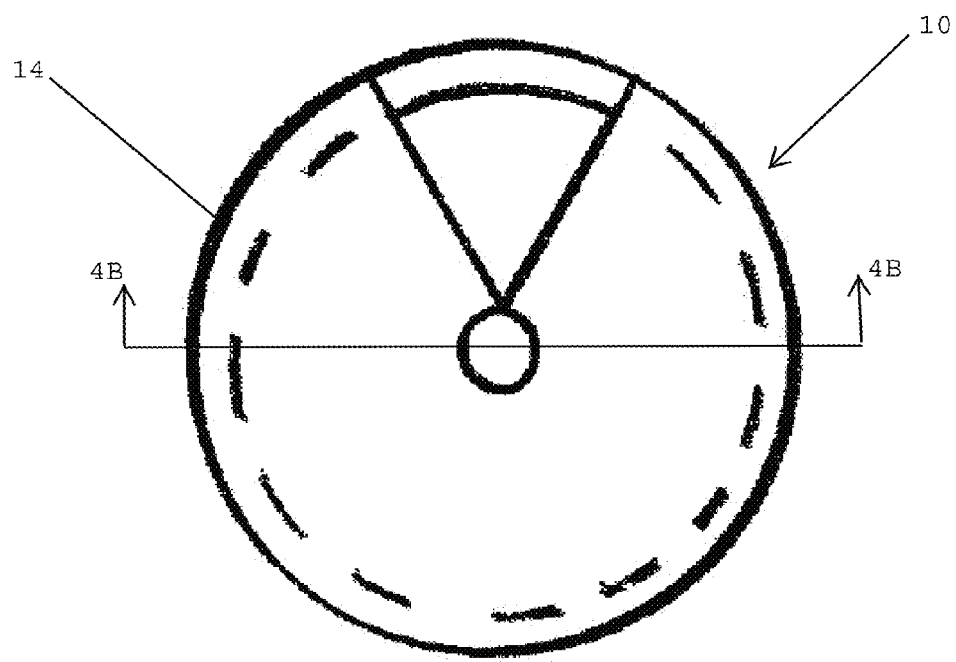
FIG. 4A shows the moveable cover of FIGS. 3A and 3B mounted atop the blood absorbing pad of FIGS. 2A and 2B, in accordance with one embodiment of the present invention.
Figure 4B:
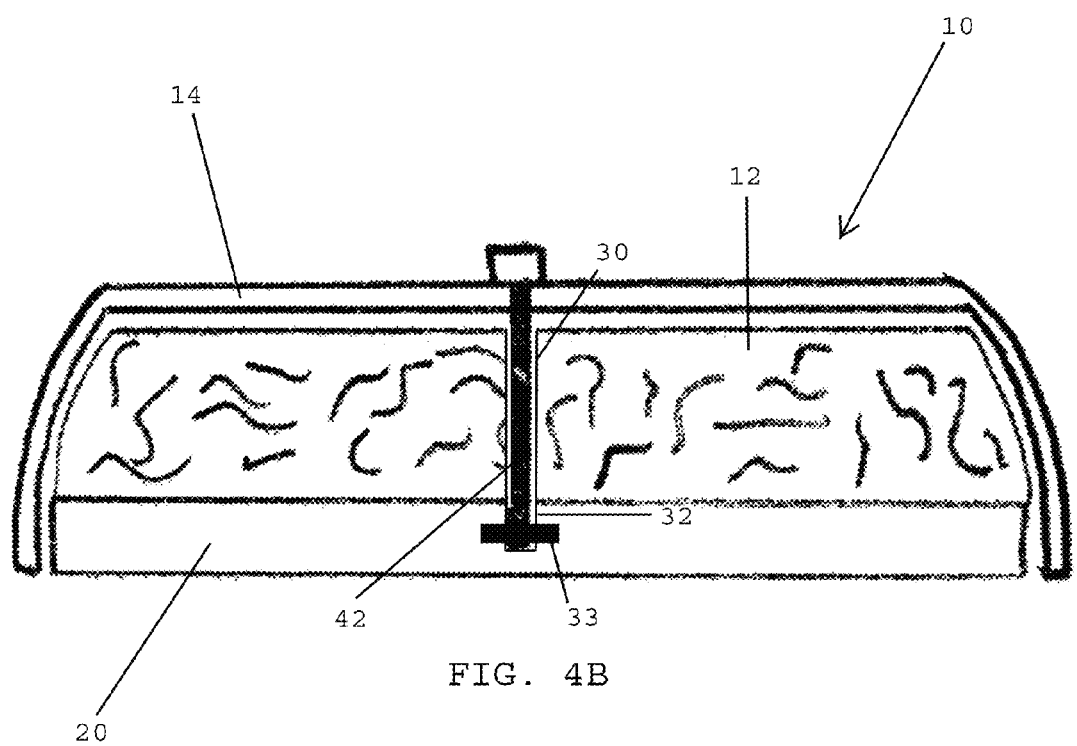
FIG. 4B shows a cross-sectional view of the moveable cover and blood absorbing pad of FIG. 4A taken along line 4B-4B thereof.

Referring to FIGS. 4A and 4B, in one embodiment, the rotatable cover 14 is assembled with the blood absorbing pad 12 and the substrate 20 by passing the shaft 42 through the central opening 30 in the blood absorbing pad 12 and the second central opening 32 in the substrate 20. The blood-blotting device 10 preferably includes a securing element 33 disposed within the substrate 20 for enabling a lower end of the shaft 42 to rotate relative to the substrate 20 while maintaining the shaft 42 connected with the substrate 20.

Figure 5A:
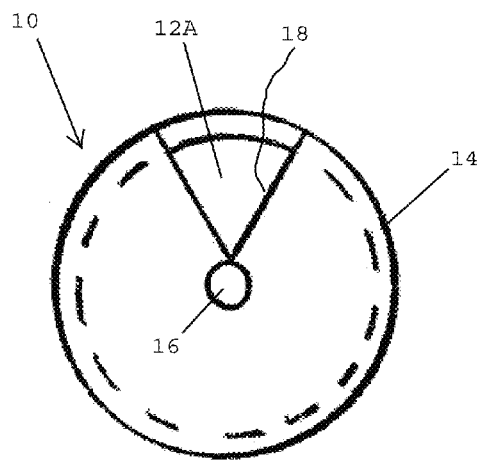
FIGS. 5A-5D show a blood-blotting device with the moveable cover at different positions for exposing different sections of a blood absorbing pad, in accordance with one embodiment of the present invention.
Figure 5B:
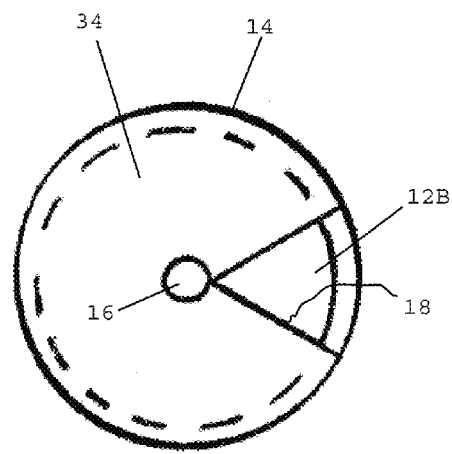

Referring to FIGS. 5A-5D, in one embodiment, the blood-blotting device 10 may be used for blotting blood from a user's fingertip. In FIG. 5A, the rotatable cover 14 is rotated to a first position so that the window 18 exposes a first blood absorbing section 12A of the blood absorbing pad. After the user has blotted his or her blood on the first section 12A, the first section 12A now has a blood stain thereon, making it desirable to rotate the cover 14 so that a fresh section of the blood absorbing pad is accessible through the window 18. Referring to FIGS. 5A and 5B, a user may engage the knob 16 and rotate the cover 14 approximately 90° in a clockwise direction to expose a second blood absorbing section 12B of the blood absorbing pad. As shown in FIG. 5B, the first blood-stained section 12A of the pad is now covered by the shell 34 of the rotatable cover 14. When a user desires to blot blood from a fingertip, the user presses the fingertip against the second blood absorbing section 12B of the blood absorbing pad.

Figure 5C:
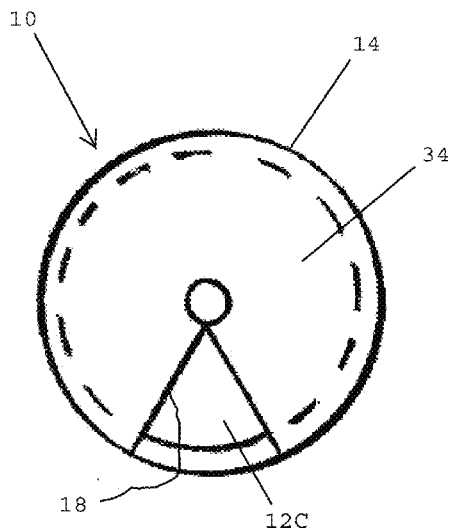

Referring to FIG. 5C, after the device 10 has been used a second time for removing blood, it is desirable to once again rotate the cover 14 in a clockwise direction (e.g. 90°) so that the window 18 is in the position shown in FIG. 5C. In FIG. 5C, the window 18 in the cover 14 exposes a third section 12C of the blood absorbing pad. The second blood absorbing section 12B, used during the step shown in FIG. 5B, is now covered by the shell 34 of the cover 14.

Figure 5D:
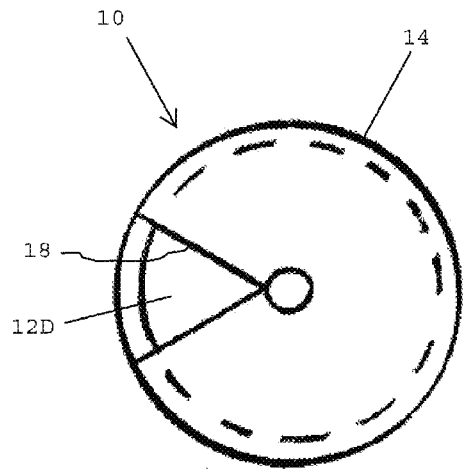

Referring to FIG. 5D, after the third use of the device 10, the cover 14 may be rotated in a clockwise direction an additional 90° to expose a fourth blood absorbing section 12D of the pad through the window 18.

FIGS. 5A-5D show four different positions for the window opening 18. In other preferred embodiments, however, the window 18 may be rotated to a greater number of positions as the cover 14 is rotated in a clockwise or counter-clockwise direction. For example, in one embodiment, the blood absorbing pad may be divided into 20 segments whereby the window 18 may be rotated into each of the 20 distinct segments for providing a clean area on the pad for blotting blood.

Figure 6:
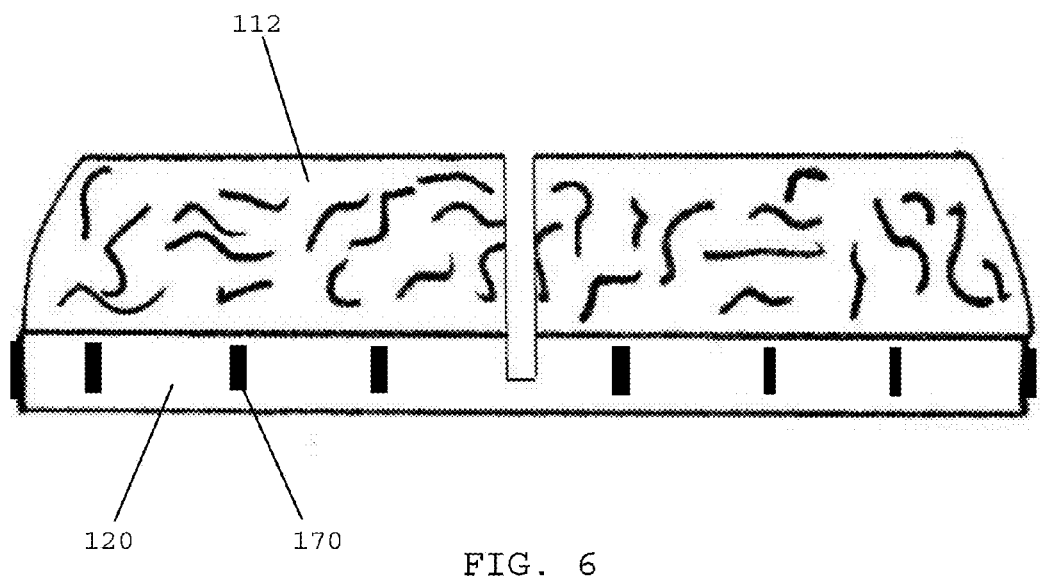
FIG. 6 shows a cross-sectional view of a blood absorbing pad and a substrate for a blood-blotting device, in accordance with one embodiment of the present invention.

Referring to FIG. 6, in one embodiment, a substrate 120 adapted to support a blood absorbing pad 112 preferably has a series of projections 170 that are evenly spaced about the outer perimeter of the substrate 120.

Figure 7:
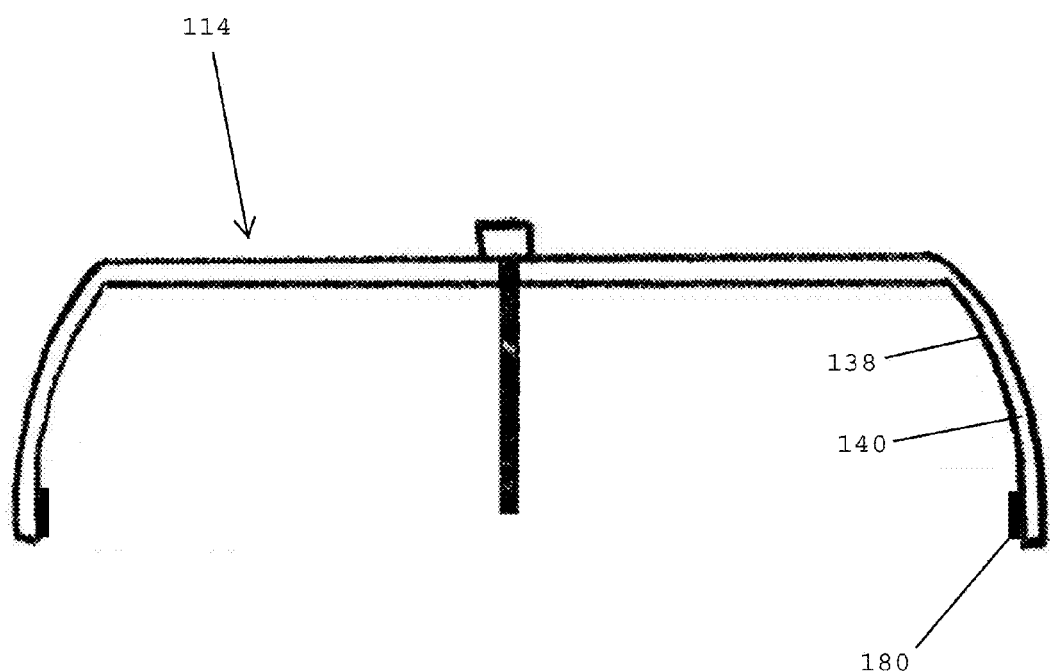
FIG. 7 shows a cross-sectional view of a cover adapted to overlie the blood absorbing pad and the substrate of FIG. 6 for forming a blood-blotting device, in accordance with one embodiment of the present invention.

Referring to FIG. 7, in one embodiment, a rotatable cover 114 preferably includes one or more inwardly extending projections 180 that project inwardly from a lateral region 140 of the shell 114. When the shell 114 is assembled over the blood absorbing pad 112 and the substrate 120, the one or more inwardly extending projections 180 on the cover 114 are preferably adapted to engage the outwardly extending projections 170 on the substrate 120. The engagement of the one or more inwardly extending projections 180 with the outwardly extending projections 170 create a frictional engagement between the cover 114 and the substrate 120, which controls rotation at the cover by enabling the cover 114 to be rotated one segment at a time in a clockwise or counter-clockwise direction. The opposing projections 170, 180 also preferably generate an audible indication, e.g. a clicking sound, so that a user will be notified that the window formed in the cover 114 has been rotated to the next section of the blood absorbing pad 112.

Although the embodiments shown in FIGS. 6 and 7 are not limited to any particular theory of operation, it is believed that the projections 170, 180 will provide an audible feedback signal in the form of a clicking sound that notifies an operator when the cover has been rotated to the next segment on the pad. The projections 170, 180 also desirably hold the window within a distinct section of the blood absorbing pad. Thus, a user does not have to worry about the cover 114 rotating freely relative to the blood absorbing pad. The projections preferably hold the window within a particular section of the pad until it is desirable to rotate the window to the next section of the pad.

Figure 8A:
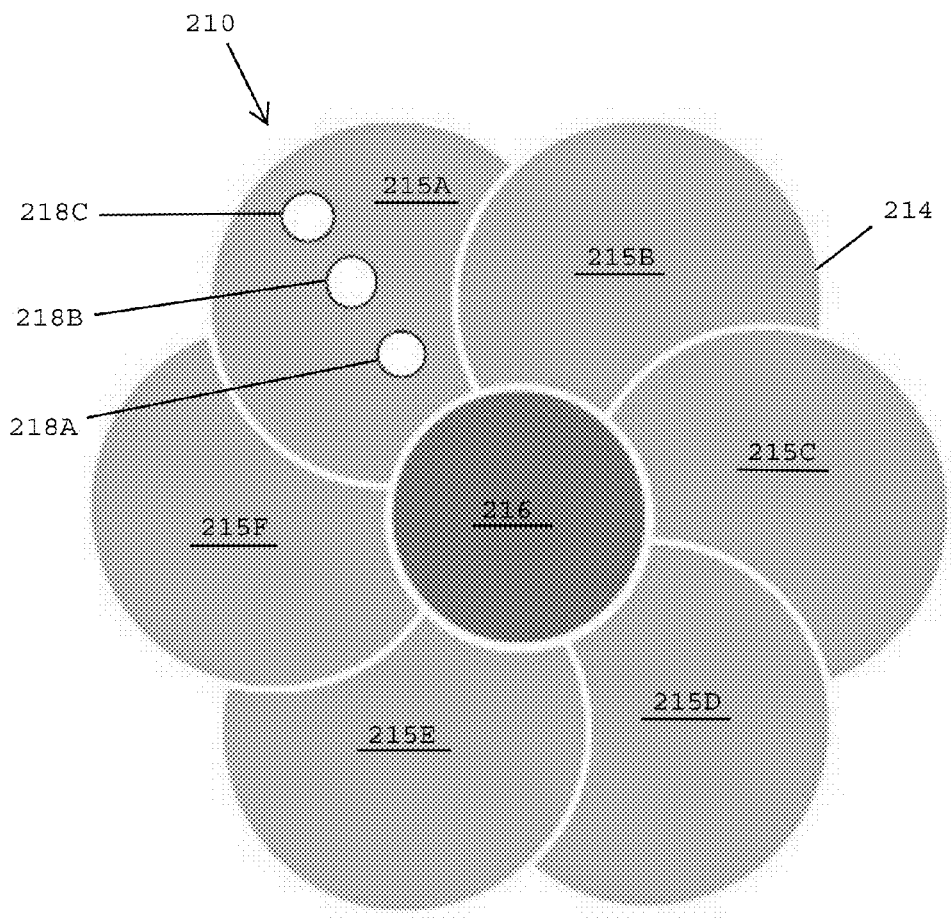
FIG. 8A shows a top plan view of a multiple-use blood-blotting device including a blood absorbing pad and a moveable flower-shaped cover overlying the blood absorbing pad, in accordance with one embodiment of the present invention.
Figure 8B:
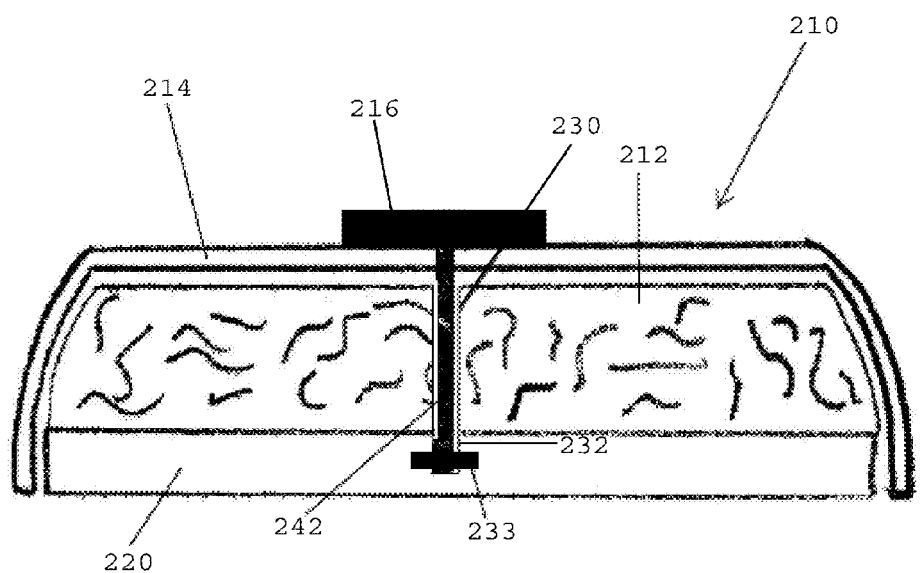
FIG. 8B shows a cross-sectional view of the multiple-use blood-blotting device of FIG. 8A.

Referring to FIGS. 8A and 8B, in one embodiment, a multiple-use blood-blotting device 210 for blotting blood on fingertips has a moveable cover 214 having the shape and appearance of a flower with petals. The flower-shaped cover 214 desirably provides an aesthetically pleasing appearance that makes the device more attractive and gratifying to use. The blood-blotting device 210 preferably includes a blood absorbing pad 212 and the moveable flower-shaped cover 214 that overlies the blood absorbing pad 212. The moveable cover 214 preferably has a knob 216 that may be engaged for moving the cover 214 relative to the blood absorbing pad 212. In one embodiment, the cover is rotated relative to the blood absorbing pad 212.

In one embodiment, the flower-shaped cover 214 has a plurality of petals 215A-215F that extend around the central knob 216. In one embodiment, a first flower petal 215A preferably has a series of windows 218A-218C that extend outwardly from the central knob 216. The first flower petal 215A preferably has an inner window 218A that exposes an interior section of the blood absorbing pad 212, an intermediate window 218B that exposes an intermediate section of the blood absorbing pad 212, and an outer window 218C that exposes an outer section of the blood absorbing pad 212. In one embodiment, the first flower petal 215A may have only one window for accessing the blood absorbing pad, two windows, or three or more windows. In one embodiment, each of the flower petals 215A-215F may have one or more windows for providing access to the underlying blood absorbing pad 212.

As will be described in more detail herein, the flower-shaped cover 214 may be rotated in clockwise or counter-clockwise directions relative to the blood absorbing pad 212 for exposing different sections of the blood absorbing pad through the respective windows 218A-218C. In one embodiment, the inner window 218A may be used for blotting blood using the interior region of the pad 212. After the inner window 218A has been rotated to different positions about 360°, the user may preferably employ the intermediate window 218B for blotting blood from the intermediate region of the pad 212. After the intermediate window 218B has been rotated to different positions about 360°, the user may preferably employ the outer window 218C for blotting blood from the outer region of the blood absorbing pad 212.

In one embodiment, after one of the windows 218A-218C has been used to blot blood, the flower-shaped cover 214 may be rotated so that another flower petal (e.g. petal 215F), adjacent to the first flower petal 215A covers the blood-stained section of the blood absorbing pad, thereby masking an unsightly blood mark. The windows 218A-218C may be rotated to overlie a fresh, unused section of the blood absorbing pad, which enhances the overall aesthetic appearance of the device. Covering the blood stained section of the pad also minimizes the likelihood that the blood will contaminate the testing equipment, or other items stored within the testing kit.

Referring to FIG. 8B, the flower-shaped cover 214 preferably includes the central knob 216 secured to a shell 234 and a shaft 242 having an upper end secured to the shell for moving (e.g. rotating) simultaneously with the shell. The knob 216 and the shaft 242 desirably rotate simultaneously with the cover 214.

Referring to FIG. 8B, in one embodiment, the flower-shaped cover 214 is assembled with the blood absorbing pad 212 and the substrate 220 by passing the shaft 242 through the central opening 230 in the blood absorbing pad 212 and the second central opening 232 in the substrate 220. The blood-blotting device 210 preferably includes a securing element 233 disposed within the substrate 220 for enabling a lower end of the shaft 242 to rotate relative to the substrate 220 while maintaining the shaft 242 connected with the substrate 220.

Figure 9A:
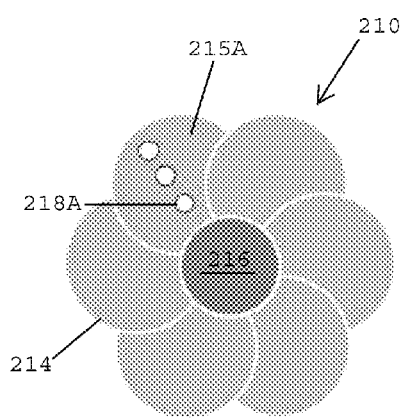
FIGS. 9A-9D show the blood-blotting device of FIGS. 8A-8B with the moveable cover at different positions for exposing different sections of a blood absorbing pad, in accordance with one embodiment of the present invention.
Figure 9B:
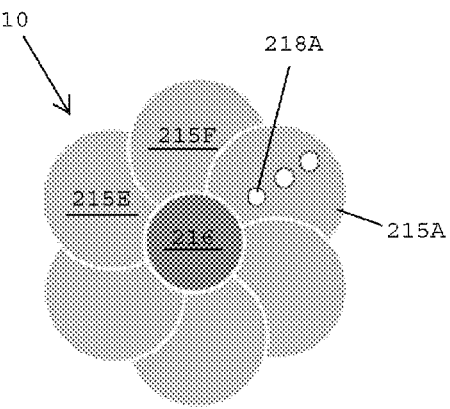

Referring to FIGS. 9A-9E, in one embodiment, the blood-blotting device 210 may be used for blotting blood from a fingertip. In FIG. 9A, the rotatable cover 214 is rotated to a first position so that the inner window 218A on the first petal 215A exposes a first interior region of the blood absorbing pad. After the user has blotted his or her blood on the first interior region of the pad, the first interior region now has a blood stain thereon, making it desirable to rotate the cover 214 so that a fresh interior section of the blood absorbing pad is accessible through the inner window 218A. Referring to FIGS. 9A and 9B, a user may engage the central knob 216 and rotate the cover 214 in a clockwise direction to expose a second interior region of the blood absorbing pad. As shown in FIG. 9B, the first interior region of the pad, which is blood stained, is now covered by the fifth and sixth petals 215E, 215F of the rotatable cover 214. When a user desires to blot blood from a fingertip, the user passes the bloody fingertip through the interior window 218A and against the second interior region of the blood absorbing pad.

Figure 9C:
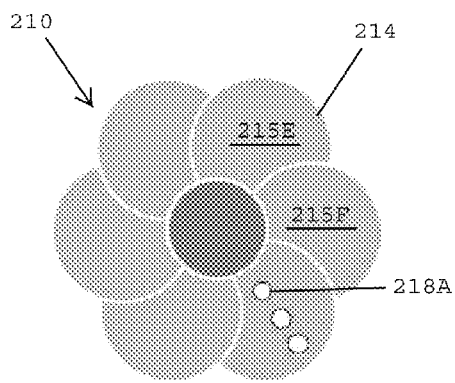
Figure 9D:
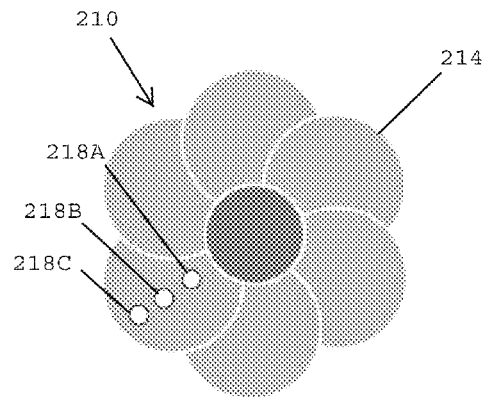

Referring to FIG. 9C, after the device 210 has been used a second time for removing blood, it is desirable to once again rotate the cover 214 in a clockwise direction (e.g. 90°) so that the inner window 218A is in the position shown in FIG. 9C. In FIG. 9C, the inner window 218A in the cover 214 exposes a third interior region of the blood absorbing pad. The second interior region used during the step shown in FIG. 9B, is now covered by flower petals 215E and 215F. Referring to FIG. 9D, after the third use of the device 210, the cover 214 may be rotated in a clockwise direction to expose a fourth interior blood absorbing section of the pad through the interior window 218A.

In one embodiment, in a similar manner as described for FIGS. 9A-9D, the intermediate window 218B may be used to blot blood using the intermediate section of the blood absorbing pad, and the outer window 218C may be used to blot blood from the outer section of the blood absorbing pad.

FIGS. 9A-9D show four separate angular positions for the inner window 218A. In other preferred embodiments, however, the inner window 218A may be rotated to a greater number of positions around the device 210. For example, in one embodiment, the interior region of the blood absorbing pad may be divided into 20 interior blood-blotting segments, 20 intermediate blood-blotting segments, and 20 outer blood-blotting segments, whereby each of the windows 218A-218C may be rotated into each of the 20 distinct segments for providing a clean area on the respective inner, intermediate, and outer sections of the blood absorbing pad for blotting blood. Thus, in one embodiment, the blood-blotting device may be used at least 60 times for blotting blood from fingertips.

In one embodiment, more two or more of the flower petals 215A-215F may have one or more windows formed therein for blotting blood. In one embodiment, each of the flower petals 215A-215F has one or more windows for blotting blood.

Figure 10:
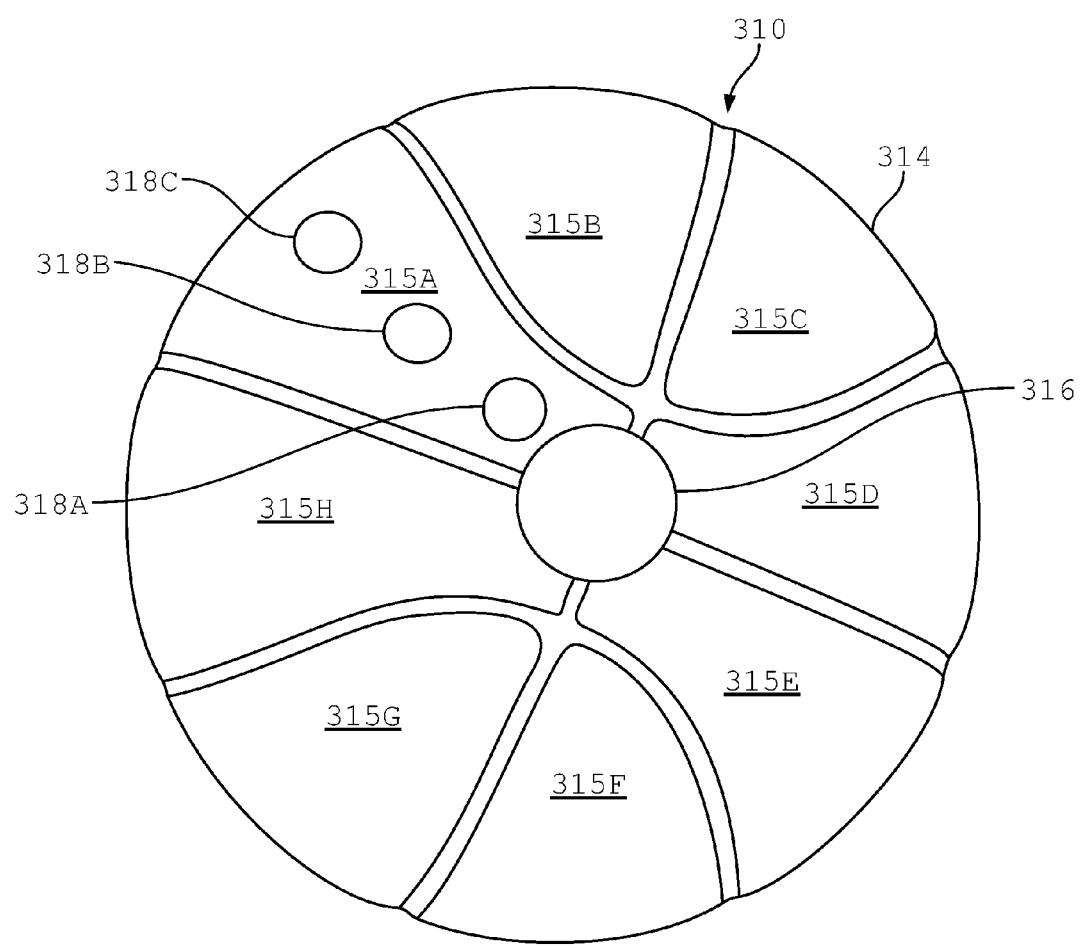
FIG. 10 shows a top plan view of a multiple-use blood-blotting device including a blood absorbing pad and a moveable basketball-shaped cover overlying the blood absorbing pad, in accordance with one embodiment of the present invention.

Referring to FIG. 10, in one embodiment, a multiple-use blood-blotting device 310 for blotting blood on fingertips has a moveable cover 314 having the shape and appearance of a basketball. The basketball shaped cover 314 desirably provides an aesthetically pleasing appearance for sports fans that makes the device more attractive and gratifying to use. The blood-blotting device 310 preferably includes a blood absorbing pad and the moveable basketball-shaped cover 314 that overlies a blood absorbing pad. The moveable cover 314 preferably has a knob 316 that may be engaged for moving the cover 314 relative to the blood absorbing pad. In one embodiment, the cover is rotated relative to the blood absorbing pad.

In one embodiment, the basketball-shaped cover 314 has a plurality of sections 315A-315H that extend around the central knob 216. In one embodiment, a first section 315A preferably has a series of windows 318A-318C that extend outwardly from the central knob 316. The first section 315A of the cover preferably has an inner window 318A that exposes an interior section of the blood absorbing pad, an intermediate window 318B that exposes an intermediate section of the blood absorbing pad, and an outer window 318C that exposes an outer section of the blood absorbing pad. The basketball-shaped cover 314 may be rotated in clockwise or counter-clockwise directions relative to the blood absorbing pad for exposing different sections of the blood absorbing pad through the respective windows 318A-318C, in a manner similar to the steps described herein for the flower-shaped cover shown in FIGS. 8A-8B and 9A-9D. FIG. 10 shows a basketball shaped cover, however, in other embodiments, other sports themed covers may be used such as baseball-shaped covers, soccer ball shaped covers, hockey puck shaped covers, etc.

Figure 11:
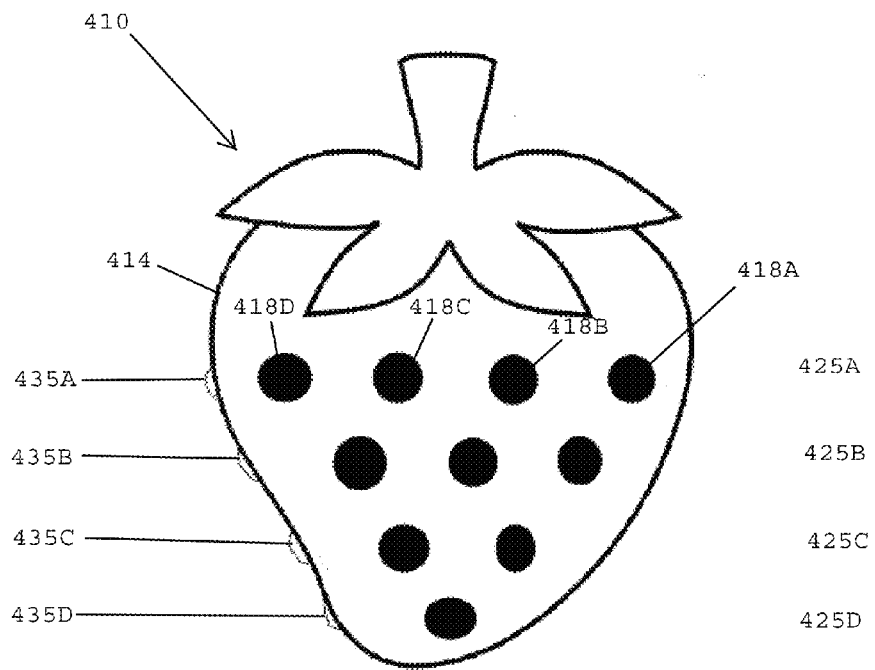
FIG. 11 shows a top plan view of a multiple-use blood-blotting device including a blood absorbing pad and a strawberry-shaped cover having a plurality of windows and sliding elements overlying the blood absorbing pad, in accordance with one embodiment of the present invention.

Referring to FIG. 11, in one embodiment, a blood-blotting device 410 desirably includes a blood absorbing pad (not shown) as described herein and a cover 414 having the shape and appearance of a strawberry. The strawberry shaped cover 414 has a first series of windows 418A-418D in a first row 425A, a second series of windows in a second row 425B, a third series of windows in a third row 425C, and a fourth series of windows in a fourth row 425D. Each of the windows preferably covers a different section of the blood absorbing pad.

Figure 12A:
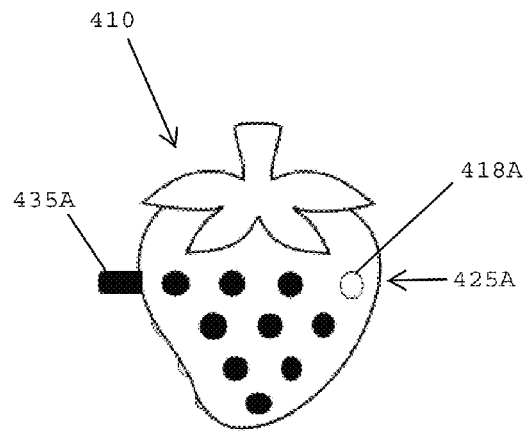
FIGS. 12A-12B show the blood-blotting device of FIG. 11 with one of the sliding elements at different positions for exposing different sections of the blood absorbing pad, in accordance with one embodiment of the present invention.

The blood-blotting device 410 preferably includes a sliding element 435A-435D associated with each of the respective rows 425A-425D. The sliding element are desirably retractable for exposing the blood absorbing pad through one or more of the windows (i.e. windows 418A-418D). Referring to FIG. 12A, in one embodiment, the first sliding element 435A is retracted to expose a section of the blood absorbing pad associated with the first window 418A in the first row 425A. After the section of the pad associated with the first window 418A has been used for blotting blood, the user may return the first sliding element 435A to the position shown in FIG. 11. The next time the user desires to blot blood using the device 410, the user may retract the first slide 435A to the position shown in FIG. 12B for exposing a fresh section of the blood absorbing pad associated with the second window 418B in the first row 425A. After the section of the pad associated with the second window 418B has been used for blotting blood, the user may return the first sliding element 435A to the position shown in FIG. 11 for covering the blood stained section on the pad.

The device may be used until all of the windows have been used for blotting blood. In one embodiment, all of the windows 418A-418D in the first row 425A are used, followed by all of the windows in the second row 425B, followed by all of the windows in the third row 425C, etc.

Figure 12B:
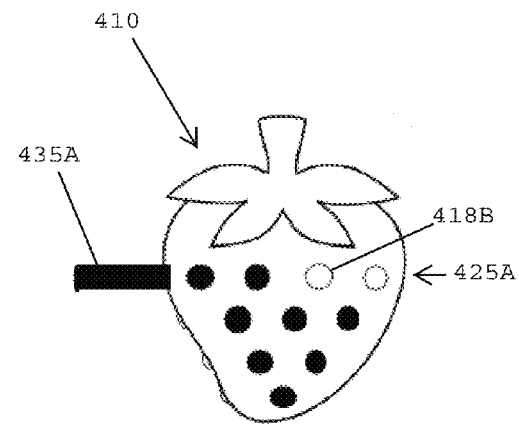

FIGS. 11 and 12A-12B show a cover 414 having sliding elements 435A-435D that may be selectively moved for exposing the blood absorbing pad through a series of different windows provided on the cover, whereby the cover has the shape and appearance of a strawberry. These drawing figures merely show one embodiment of the present invention. In other embodiments, a cover having selectively moveable sliding elements associated with respective rows of windows may have other shapes and configurations such as a vehicle (e.g. a truck, a space ship), an animal (e.g. a horse, a cow), or a fruit (an apple, an orange).

In one embodiment, a blood-blotting device includes a cover having an array of windows, with each window being associated with a different section of a blood absorbing pad. The device includes one or more sliding elements that may be retracted for exposing the blood absorbing pad through one or more of the windows in the cover. The sliding elements are preferably disposed between the cover and the blood absorbing pad. One or more of the sliding elements may have a knob at an end thereof that is accessible at an outer perimeter of the cover for moving the sliding elements relative to the cover for exposing the different sections of the blood absorbing pad.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A multiple-use blotting device for blotting blood from a fingertip comprising:
    a substrate;
    a blood absorbing pad secured atop said substrate, said blood absorbing pad having a plurality of blood absorbing sections, wherein said substrate comprises a top surface and said blood absorbing pad is secured to the top surface of said substrate;
    a cover overlying said blood absorbing pad, said cover having at least one window formed therein for exposing one of said blood absorbing sections, wherein said cover is moveable relative to said blood absorbing pad for exposing a fresh section of said blood absorbing pad through said at least one window while covering a previously used section of said blood absorbing pad.

2. The multiple-use blotting device as claimed in claim 1, wherein said at least one window comprises a single window formed in said cover for exposing one of said blood absorbing sections, wherein said cover is rotatable relative to said blood absorbing pad for exposing only one of said blood absorbing sections at a time while covering the remaining blood absorbing sections of said blood absorbing pad.

3. The multiple-use blotting device as claimed in claim 2, wherein said blood absorbing sections are spaced from one another on said blood absorbing pad.

4. The multiple-use blotting device as claimed in claim 3, wherein said blood absorbing sections are evenly spaced from one another around a perimeter of said blood absorbing pad.

5. The multiple-use blotting device as claimed in claim 2, wherein said cover has a circular shape, and wherein said window extends between a center of said cover and an outer perimeter of said cover.

6. The multiple-use blotting device as claimed in claim 2, wherein said cover comprises:
    a shell having said window formed therein; and
    a knob provided on a top surface of said shell, wherein said knob is engageable for rotating said shell for sequentially aligning said window with each of said blood absorbing sections.

7. The multiple-use device as claimed in claim 6, further comprising a shaft extending through said blood absorbing pad, said shaft having an upper end coupled with said shell and a lower end coupled with said substrate.

8. The multiple-use device as claimed in claim 7, wherein said cover, said knob and said shaft rotate simultaneously with one another, and wherein said cover, said knob and said shaft are rotated relative to said blood absorbing pad and said substrate.

9. The multiple-use device as claimed in claim 1, wherein said cover and said substrate comprise polymer materials and said blood absorbing pad comprises cotton or fiber.

10. The multiple-use blotting device as claimed in claim 1, wherein said blood absorbing pad has a top surface accessible through said at least one window of said cover.

11. The multiple-use blotting device as claimed in claim 1, wherein said blood absorbing pad has a porous cover.

12. The multiple-use blotting device as claimed in claim 1, wherein said blood absorbing pad comprises an antibacterial agent, a germicidal agent, a disinfectant, or a moisturizer.

13. The multiple-use blotting device as claimed in claim 2, wherein said substrate has a side wall that extends around a perimeter of said substrate and a plurality of projections that extend outwardly from said side wall, and wherein said cover has an inner surface having at least one projection adapted to engage said side wall projections of said substrate for generating an audible sound when said cover projection passes over one of said substrate projections.

14. A multiple-use blotting device for blotting blood from a fingertip comprising:
    a substrate having a top surface;
    a blood absorbing pad secured over the top surface of said substrate, said blood absorbing pad having a plurality of blood absorbing sections that are spaced from one another on said blood absorbing pad;
    a protective cover overlying said blood absorbing pad, said protective cover having a plurality of windows formed therein that are associated with said plurality of blood absorbing sections of said blood absorbing pad, wherein said cover is coupled with said substrate and is adapted to move relative to said substrate and said blood absorbing pad for selectively aligning said windows with each of said blood absorbing sections, and wherein said protective cover comprises a shell having a knob provided at a top surface of said shell, and wherein said device further comprises a shaft used for forming a moveable connection between said shell and said substrate, said shaft having an upper end coupled with said shell and a lower end coupled with said substrate.

15. The multiple-use blotting device as claimed in claim 14, wherein said blood absorbing pad and said protective cover have circular shapes, wherein said protective cover is rotatable relative to said blood absorbing pad, and wherein said windows are located between a center of said protective cover and an outer perimeter of said protective cover.

16. The multiple-use blotting device as claimed in claim 14, wherein said protective cover includes a first inner window overlying an interior region of said blood absorbing pad, and a second intermediate window covering an intermediate region of said blood absorbing pad, and wherein said protective cover is rotatable in clockwise and counterclockwise directions for exposing, one at a time, each of said blood absorbing sections through said windows.

17. The multiple-use blotting device as claimed in claim 14, wherein said device has a diameter of about 3-5 inches and a thickness of about 0.10-1.00 inches.

18. A multiple-use blotting device for blotting blood from a fingertip comprising:
   a substrate having a top surface;
   a blood absorbing pad secured over the top surface of said substrate, said blood absorbing pad having a plurality of blood absorbing sections that are spaced from one another on said blood absorbing pad;
   a protective cover overlying said blood absorbing pad, said protective cover having a plurality of windows formed therein that are associated with said plurality of blood absorbing sections of said blood absorbing pad;
   at least one sliding element disposed between said protective cover and said blood absorbing pad, wherein said sliding element is retractable from a first position to a second position for exposing at least one of said blood absorbing sections through at least one of said windows, and wherein said sliding element is moveable from the second position back to the first position for recovering the at least one of said blood absorbing sections exposed through the at least one of said windows.

* * * * *